United States Patent
Kwon et al.

(10) Patent No.: US 7,189,948 B2
(45) Date of Patent: Mar. 13, 2007

(54) METHOD FOR CONTROLLING THE HEATING OF AN OXYGEN SENSOR FOR AN ENGINE OF A VEHICLE

(75) Inventors: Young Soo Kwon, Suwon (KR); Jong Seok Yoon, Seongnam (KR); Ki Ha Shin, Ulsan (KR)

(73) Assignee: Hyundai Motor Company, Seoul (KR)

( * ) Notice: Subject to any disclaimer, the term of this patent is extended or adjusted under 35 U.S.C. 154(b) by 321 days.

(21) Appl. No.: 10/747,903

(22) Filed: Dec. 29, 2003

(65) Prior Publication Data
US 2005/0082279 A1   Apr. 21, 2005

(30) Foreign Application Priority Data
Oct. 15, 2003   (KR)   ........................ 10-2003-0071786

(51) Int. Cl.
*H05B 1/02* (2006.01)
(52) U.S. Cl. .................... 219/497; 219/202; 60/286
(58) Field of Classification Search ................ 219/497, 219/501, 505, 494, 202; 60/285, 286, 272, 60/276
See application file for complete search history.

(56) References Cited

U.S. PATENT DOCUMENTS

| 6,003,307 A * | 12/1999 | Naber et al. .................. 60/274 |
| 6,363,715 B1 * | 4/2002 | Bidner et al. .................. 60/285 |
| 2003/0010016 A1 * | 1/2003 | Beer et al. .................... 60/274 |

FOREIGN PATENT DOCUMENTS

| DE | 197 29 350 A1 | 1/1998 |
| JP | 2002-021631 | 1/2002 |
| KR | 10-1999-0059847 | 7/1999 |

* cited by examiner

*Primary Examiner*—Mark Paschall
(74) *Attorney, Agent, or Firm*—Morgan Lewis & Bockius LLP

(57) ABSTRACT

A lower limit of a heating factor for heating control of an oxygen sensor is adjusted on the basis of the heating factor, a P-jump delay time calculated based on an output voltage of the oxygen sensor, and a diagnosis index of the oxygen sensor, and thereby an engine may be stably controlled even if the oxygen sensor is aged.

12 Claims, 2 Drawing Sheets

METHOD FOR CONTROLLING THE HEATING OF AN OXYGEN SENSOR FOR AN ENGINE OF A VEHICLE

CROSS-REFERENCE TO RELATED APPLICATIONS

This application claims priority of Korean Application No. 10-2003-0071786, filed on Oct. 15, 2003, the disclosure of which is incorporated fully herein by reference.

FIELD OF THE INVENTION

The present invention relates generally to vehicles. More particularly, the present invention relates to a method for controlling the heating of an oxygen sensor for an engine of a vehicle.

BACKGROUND OF THE INVENTION

In order to reduce noxious exhaust gas emissions from a vehicle, fuel injection is controlled on the basis of output signals from an oxygen sensor ($O_2$ sensor). For example, when the output voltage of the oxygen sensor is low (i.e., when an air/fuel ratio is lean), P-jump delay time for fuel injection control is increased such that more fuel is injected into the engine.

For normal operation of an oxygen sensor, the temperature of the oxygen sensor should be maintained at an appropriate activation temperature. In the case where the activation temperature is not maintained by the exhaust gas from the engine (e.g., just after the engine has been started), the oxygen sensor is actively heated. During such controlled heating of the oxygen sensor, an electric heater provided in the oxygen sensor is duty controlled.

The duty (hereinafter referred to as "heating duty") for controlling the heating of the oxygen sensor is obtained by multiplying a feedback factor (hereinafter referred to as a "heating factor") to a base duty calculated on the basis of engine speed and engine load. That is, the heating factor is P-I (proportionally-integrationally) controlled on the basis of the output voltage of the oxygen sensor, so that the oxygen sensor is feedback controlled.

According to the prior art, such a heating factor is only increased or decreased simply on the basis of the output voltage of the oxygen sensor. However, when an oxygen sensor is aged (e.g., heat-aged), it may produce a malfunction that can not be compensated by the prior art. One typical example of such an oxygen sensor malfunction is a switching time error, in which the switching time needed for the sensor to detect a transition from a lean to a rich A/F ratio, or vice versa, exceeds a threshold switching time. A switching time index is calculated as the ratio of the switching time to the threshold switching time, and the occurrence of a switching time error is determined on the basis of whether the switching time index is greater than a predetermined threshold index.

Another example of an oxygen sensor malfunction is a frequency characteristic error in which the frequency characteristic of the output voltage of the oxygen sensor does not reach a threshold frequency. A frequency index is calculated as being proportional to the reciprocal of the frequency, and the frequency characteristic error is determined on the basis of whether the frequency index is greater than a predetermined threshold frequency index. For example, according to non-opened experiments and regarding aged oxygen sensors of a Titania type, the switching time index and the frequency index have been found to became very high while the heating factor is controlled low. In addition, in this case, the P-jump delay time has been found to become a very large value. That is, when an oxygen sensor is heat-aged, the switching time index and the frequency index may become deteriorated at the same time that excessive fuel injection occurs. However, according to a heating control of an oxygen sensor of the prior art, normal operation of the oxygen sensor is premised such that only minimal heating of the oxygen sensor is performed.

SUMMARY OF THE INVENTION

An exemplary method according to an embodiment of the present invention controls heating of an oxygen sensor of an engine of a vehicle on the basis of a heating factor having a lower limit, and includes setting the heating factor as a base value upon starting of the engine, calculating an average voltage of the oxygen sensor, determining if the average voltage of the oxygen sensor is less than a predetermined reference voltage, decreasing the heating factor when the average voltage of the oxygen sensor is less than the reference voltage, and adjusting the lower limit of the heating factor on the basis of the decreased heating factor, a P-jump delay time calculated based on an output voltage of the oxygen sensor, and at least one diagnosis index of the oxygen sensor.

In a further embodiment, the step of adjusting the lower limit of the heating factor comprises determining if a first predetermined condition regarding the heating factor is satisfied, determining if a second predetermined condition regarding the P-jump delay time and the at least one oxygen sensor diagnosis index is satisfied, and resetting the lower limit of the heating factor to the base value when the first and second predetermined conditions are satisfied.

In a still further embodiment, the first predetermined condition comprises the heating factor being less than a reference factor that is below the base value.

In a still further embodiment, the predetermined reference factor is about 0.65.

In a still further embodiment, the step of determining if a second predetermined condition is satisfied comprises calculating the P-jump delay time on the basis of the output voltage of the oxygen sensor, and calculating the diagnosis index of the oxygen sensor, wherein the second predetermined condition is satisfied when the P-jump delay time is greater than a predetermined reference delay time or the diagnosis index of the oxygen sensor is greater than a first predetermined ratio of a predetermined threshold index.

In a still further embodiment, the first predetermined ratio is about 50%.

In a still further embodiment, the method further includes determining if a third predetermined condition regarding the oxygen sensor diagnosis index and a coolant temperature of the engine is satisfied, and maintaining the lower limit of the heating factor as a predetermined factor value for a predetermined period when the third predetermined condition is satisfied, the predetermined factor value being greater than the base value.

In a still further embodiment, the predetermined factor value is about 1.25 and the predetermined period is about 45 seconds.

In a still further embodiment, the third predetermined condition comprises the oxygen sensor diagnosis index being greater than a second predetermined ratio of the predetermined threshold index, and the coolant temperature of the engine being less than a predetermined reference temperature.

In a still further embodiment, the second predetermined ratio is about 80%.

In a still further embodiment, the reference voltage lies between rich and lean regions of an air/fuel ratio.

In a yet still further embodiment, the reference voltage is as about 2.5V or about 0.5V.

BRIEF DESCRIPTION OF THE DRAWINGS

The accompanying drawings, which are incorporated in and constitute a part of the specification, illustrate an embodiment of the invention, and, together with the description, serve to explain the principles of the invention, wherein.

DETAILED DESCRIPTION OF THE PREFERRED EMBODIMENTS

Figure 1:
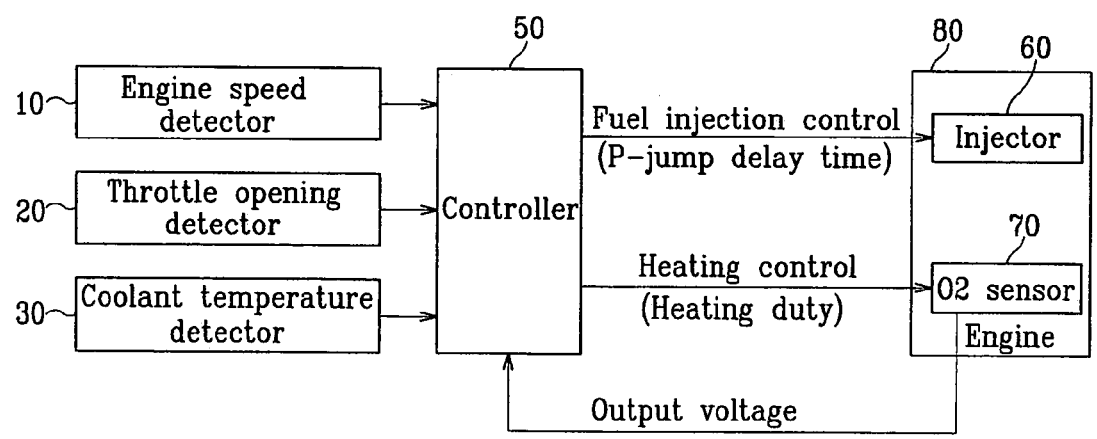
FIG. 1 is a block diagram showing an apparatus for controlling the heating of an oxygen sensor for an engine of a vehicle according to an illustrative embodiment of the present invention.

An embodiment of the present invention will hereinafter be described in detail with reference to the accompanying drawings. As shown in FIG. 1, an illustrative apparatus for controlling heating of an oxygen sensor for an engine of a vehicle controls the heating of an oxygen sensor 70 included in the engine 80. The engine 80 is provided with an injector 60 that injects fuel into the engine 80. The apparatus of the present invention may also include an engine speed detector 10 for detecting the current speed of the engine 80, a throttle opening detector 20 for detecting the throttle valve opening of the engine 80, a coolant temperature detector 30 for detecting the coolant temperature of the engine 80, and a controller 50 for controlling heating of the oxygen sensor 70 on the basis of signals from the detectors 10, 20, and 30, and the output voltage of the oxygen sensor 70.

The controller 50 also controls the amount of fuel injection done by the injector 60, on the basis of signals from the detectors 10, 20, and 30, and the output voltage of the oxygen sensor 70. During the fuel controlling process, the controller 50 calculates a P-jump delay time and uses it to control the amount of fuel injection. The fuel injection control function performed by controller 50 may be achieved by a conventional scheme known to a person of ordinary skill in the art.

The controller 50 may include one or more processors activated by a predetermined program. The program may perform each step of the following method, which will now be described in detail with reference to FIG. 2.

Figure 2:
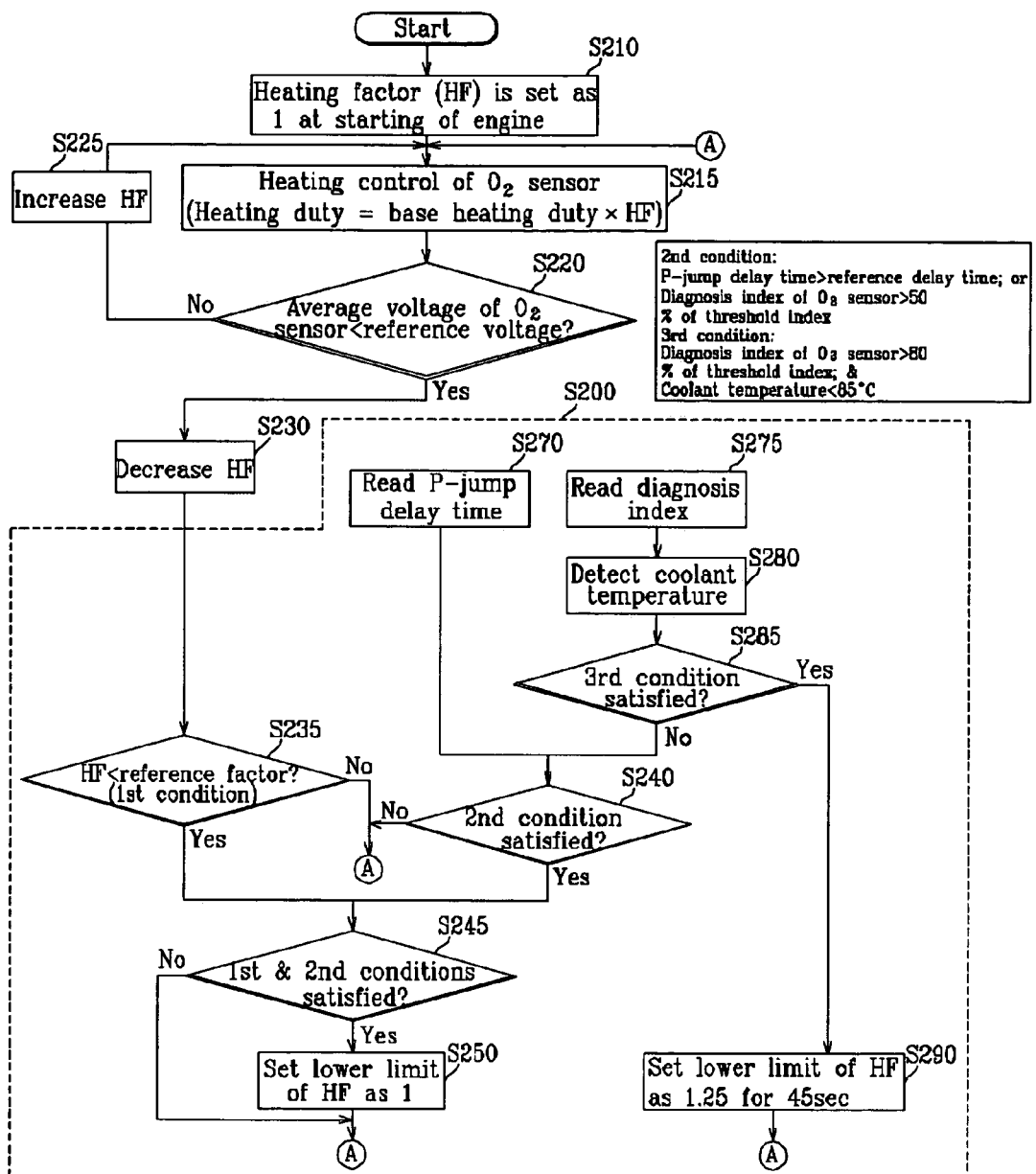
FIG. 2 is a block diagram showing a method for controlling the heating of an oxygen sensor for an engine of a vehicle according to an embodiment of the present invention.

Turning to FIG. 2, a heating factor HF described in the following description has a lower limit, such that the calculated heating factor HF should not be lower than the lower limit. The lower limit may be varied during execution of the present method.

Upon starting of the engine 80, the controller 50 sets the heating factor HF for activation of the oxygen sensor 70 as a base value (e.g., 1) at step S210. Then, at step S215, the controller 50 controls the heating of the oxygen sensor 70 on the basis of the heating factor HF. At step S215, the controller 50 controls the oxygen sensor 70 based on a heating duty calculated by multiplying the heating factor HF by a base value. The base value is determined on the basis of the engine speed and the engine load (e.g., throttle valve opening).

At step S220, the controller 50 determines if the average value of the output voltage from the oxygen sensor 70 is less than a predetermined reference voltage. The reference voltage may be preset depending on the type of oxygen sensor used. For example, the reference voltage is preferably set as about 2.5V for an oxygen sensor of a Titania type, and is preferably set as about 0.5V for an oxygen sensor of a Zirconia type. Such a reference voltage is usually preset so as to lie between rich and lean ranges of the air/fuel ratio. For example, the reference voltage is preset as a value that lies within a range from 1 volt to 2 volts in the case that the output voltage of the oxygen sensor 70 becomes less than 1 volt when the air/fuel ratio is lean, and greater than 2 volts when the air/fuel ratio is rich. By setting the reference voltage as described above, the step S220 may roughly differentiate a rich or lean state of the air/fuel ratio.

When the average voltage of the oxygen sensor 70 is less than the reference voltage at step S220, the controller 50 increases the heating factor HF at step S225, and returns to step S215 to control the heating of the oxygen sensor 70 based on the increased heating factor HF. The amount of the increase in the heating factor HF at the step S225 may be determined by a person of ordinary skill in the art.

When the average voltage of the oxygen sensor 70 is not less than the reference voltage at step S220, the controller 50 decreases the heating factor HF at step S230. The amount of decrease of the heating factor HF at the step S230 may be preferably set by a person ordinarily skilled in the art. Next, at step S200, the controller 50 adjusts the lower limit of the heating factor HF on the basis of the decreased heating factor HF, the P-jump delay time calculated based on an output voltage of the oxygen sensor, and at least one diagnosis index of the oxygen sensor.

Step S200 will now be described in further detail. First, at step S235, the controller 50 determines if a first predetermined condition regarding the heating factor HF is satisfied. According to one embodiment of the present invention, the first predetermined condition is preset as the heating factor HF being less than a reference factor that is below the base value (i.e., 1). Here, the predetermined reference factor is less than the base value, and is preferably set as about 0.65.

When the first predetermined condition is not satisfied, which implies that the heating factor is not low, the controller 50 returns to the S215 to control heating of the oxygen sensor without adjusting the lower limit.

Separately from step S235 of determining if the first predetermined condition is satisfied, at step S240, the controller 50 determines if a second predetermined condition regarding the P-jump delay time and the at least one oxygen sensor diagnosis index is satisfied. According to one embodiment of the present invention, the second predetermined condition is satisfied when the P-jump delay time is greater than a predetermined reference delay time (e.g., 350 msec) or the diagnosis index of the oxygen sensor is greater than a first predetermined ratio (e.g., 50%) of a predetermined threshold index. Therefore, by step S240, the controller 50 may estimate whether fuel is excessively injected or if a possibility of malfunctioning of the oxygen sensor 70 is relatively high.

According to one embodiment of the present invention, the diagnosis index of the oxygen sensor includes both a switching time index and a frequency index. That is, the diagnosis index of the oxygen sensor is said to be greater than 50% of the threshold index when the switching time index is greater than 50% of a predetermined threshold switching time index, or when the frequency index is greater than 50% of a predetermined threshold frequency index.

As was described above, step S240 is repeatedly executed during operation of the engine 80 separately from step 235. In more detail, at step S270, the controller 50 repeatedly calculates, for the fuel control of the engine 80, the P-jump delay time on the basis of the output voltage of the oxygen sensor 70, and at step S275, it also calculates the diagnosis index of the oxygen sensor. At step S275, both the switching time index and the frequency index are calculated. By the repeated execution of steps S270 and S275, the controller 50 is always ready to check satisfaction of the second predetermined condition.

When the second predetermined condition is not satisfied at step S240, which implies that neither the P-jump delay time is high nor that the possibility of a malfunction at the oxygen sensor 70 is high, the controller 50 returns to step S215 to control heating of the oxygen sensor without adjusting the lower limit.

At step S245, the controller 50 determines if both the first and second predetermined conditions are satisfied. When one or both of the first and second predetermined conditions is not satisfied at step S245, the controller 50 returns to step S215 to control heating of the oxygen sensor without adjusting the lower limit.

When both the first and second predetermined conditions are satisfied at step 245, the controller 50 resets the lower limit of the heating factor HF to the base value at step S250.

Usually, the lower limit of the heating factor HF is initially set less than the base value. At step S250, such a lower limit is increasingly adjusted to the base value. So, after step S250, the controller 50 should control heating of the oxygen sensor 70 based on a heating duty greater than the base duty.

According to one embodiment of the present invention, at step S285, the controller 50 further determines if a third predetermined condition regarding the oxygen sensor diagnosis index and the coolant temperature of the engine 80 is satisfied. The third predetermined condition may be preset as the oxygen sensor diagnosis index being greater than a second predetermined ratio (e.g., 80%) of the predetermined threshold index, and the coolant temperature of the engine 80 being less than a predetermined reference temperature (e.g., 85° C.). After calculating the oxygen sensor diagnosis index including the switching time index and the frequency index at the above-mentioned step S275, the controller 50 detects a coolant temperature at step S280, and subsequently at step S285, determines if the third predetermined condition is satisfied by the coolant temperature and the oxygen sensor diagnosis index.

As was describe above, according to one embodiment of the present invention, the diagnosis index of the oxygen sensor includes both the switching time index and the frequency index. That is, the diagnosis index of the oxygen sensor is said to be greater than 80% of the threshold index when the switching time index is greater than 80% of a predetermined threshold switching time index, or when the frequency index is greater than 80% of a predetermined threshold frequency index.

When the third predetermined condition is satisfied, the controller 50 maintains the lower limit of the heating factor HF as a predetermined factor value (e.g., 1.25) for a predetermined period (e.g., 45 seconds). The predetermined factor value is greater than the base value. Therefore, for the predetermined period after step S290, the controller 50 should control heating of the oxygen sensor 70 by a heating duty greater than a value obtained by multiplying the base value by the base duty. Therefore, when the possibility of malfunctioning of the oxygen sensor 70 is high while the coolant temperature is low, the oxygen sensor is highly heated for a certain period so it is quickly activated.

According to one embodiment of the present invention, even if the oxygen sensor is aged or heat-aged, the engine can be stably controlled due to controlled heating of the oxygen sensor.

The following Table 1 compares the results of tests run using an illustrative embodiment of the method of the present invention, with results of tests run using a prior art method.

TABLE 1

(results from prior art method/results from method of present invention)

| | | SWT index | | FRQ index | | P-jump delay time |
|---|---|---|---|---|---|---|
| | | lean→rich | rich→lean | lean→rich | rich→lean | (msec) |
| Vehicle | B1 | 101/53 | 76/54 | 63/48 | 71/62 | 850/617 |
| type 1 | B2 | 115/57 | 75/58 | 56/52 | 72/63 | 850/583 |
| Vehicle | B1 | 92/46 | 55/33 | 38/35 | 79/69 | 850/569 |
| type 2 | B2 | 31/31 | 23/20 | 39/35 | 76/67 | 818/547 |
| Vehicle | B1 | 100/36 | 72/27 | 53/40 | 83/59 | 750/497 |
| type 3 | B2 | 81/44 | 39/34 | 44/36 | 80/55 | 760/551 |

For two vehicles B1 and B2 in each of three vehicle types (i.e., type 1, type 2, and type 3), the above Table 1 compares test results from prior art methods and the method of the present invention.

As can be seen in Table 1, according to the illustrative embodiment of the present invention, the switching time index (SWT index) is maximally enhanced by about 64%. That is, even if an oxygen sensor is aged, the switching time of the oxygen sensor is reduced by appropriate heating control thereof. In addition, the frequency index (FRQ index) is also significantly enhanced. The learned value of P-JUMP delay time is also enhanced from 850 msec of the prior art to 547–617 msec such that excessive fuel injection is prevented.

In addition, although not shown in the above table, the temperature of the oxygen sensor was also enhanced from 600±20° C. of the prior art, to a level of 700±20° C., which is closer to the activation temperature of the oxygen sensor.

The following Table 2 shows tested results of methods for controlling heating of an oxygen sensor of an engine of a vehicle according to an embodiment of the present invention and according the prior art.

The following Table 2 shows test results for an engine having an aged oxygen sensor, when heating thereof is controlled by a prior art method, and when heating is controlled by an illustrative method of the present invention.

TABLE 2

| | | NOx (result from prior art/result from present invention) |
|---|---|---|
| Vehicle type 1 | Allowable limit | 0.6 |
| | Test result | 2.05/0.41 |
| Vehicle type 2 | Allowable limit | 0.5 |
| | Test result | 0.84/0.17 |
| Vehicle type 3 | Test result | 1.12/0.23 |

As can be seen in Table 2, according to the prior art, when an oxygen sensor is aged or heat-aged, the exhaust gas of the engine contains greater than allowable amounts of nitric oxides NOx. However, according to an illustrative embodiment of the present invention, such nitric oxides NOx are significantly reduced due to controlled heating of the oxygen sensor, and thereby, the amount comes to within the allowable limit.

While this invention has been described in connection with what is presently considered to be the most practical and preferred embodiment, it is to be understood that the invention is not limited to the disclosed embodiments. Rather, the present invention is intended to cover various modifications and equivalent arrangements included within the spirit and scope of the appended claims.

What is claimed is:

1. A method for controlling heating of an oxygen sensor for an engine of a vehicle on the basis of a heating factor having a lower limit, the method comprising:
   setting the heating factor as a base value upon starting of the engine;
   calculating an average voltage of the oxygen sensor;
   determining if the average voltage of the oxygen sensor is less than a predetermined reference voltage;
   decreasing the heating factor when the average voltage of the oxygen sensor is less than the reference voltage; and
   adjusting the lower limit of the heating factor on the basis of the decreased heating factor, a P-jump delay time calculated based on an output voltage of the oxygen sensor, and at least one diagnosis index of the oxygen sensor.

2. The method of claim 1, wherein the step of adjusting the lower limit of the heating factor comprises:
   determining if a first predetermined condition regarding the heating factor is satisfied;
   determining if a second predetermined condition regarding the P-jump delay time and the at least one oxygen sensor diagnosis index is satisfied; and
   resetting the lower limit of the heating factor to the base value when the first and second predetermined conditions are satisfied.

3. The method of claim 2, wherein the first predetermined condition comprises the heating factor being less than a reference factor that is below the base value.

4. The method of claim 3, wherein the predetermined reference factor is about 0.65.

5. The method of claim 2, wherein the step of determining if a second predetermined condition is satisfied comprises:
   calculating the P-jump delay time on the basis of the output voltage of the oxygen sensor; and
   calculating the diagnosis index of the oxygen sensor,
   wherein the second predetermined condition is satisfied when the P-jump delay time is greater than a predetermined reference delay time or the diagnosis index of the oxygen sensor is greater than a first predetermined ratio of a predetermined threshold index.

6. The method of claim 5, wherein the first predetermined ratio is about 50%.

7. The method of claim 2, further comprising:
   determining if a third predetermined condition regarding the oxygen sensor diagnosis index and a coolant temperature of the engine is satisfied; and
   maintaining the lower limit of the heating factor as a predetermined factor value for a predetermined period when the third predetermined condition is satisfied, the predetermined factor value being greater than the base value.

8. The method of claim 7, wherein the predetermined factor value is about 1.25 and the predetermined period is about 45 seconds.

9. The method of claim 7, wherein the third predetermined condition comprises:
   the oxygen sensor diagnosis index being greater than a second predetermined ratio of the predetermined threshold index; and
   the coolant temperature of the engine being less than a predetermined reference temperature.

10. The method of claim 9, wherein the second predetermined ratio is about 80%.

11. The method of claim 1, wherein the reference voltage lies between rich and lean regions of an air/fuel ratio.

12. The method of claim 11, wherein the reference voltage is about 2.5V or about 0.5V.

* * * * *